(12) United States Patent  (10) Patent No.: US 7,157,574 B2
Matsumoto et al.  (45) Date of Patent: Jan. 2, 2007

(54) PROCESS FOR PREPARING CRYSTALLINE 3-CHLOROMETHYL-3-CEPHEM DERIVATIVES

(75) Inventors: Nobuo Matsumoto, Tokyo (JP); Hiroshi Kawakabe, Tokyo (JP); Yasuko Manabe, Tokyo (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 356 days.

(21) Appl. No.: 10/808,600

(22) Filed: Mar. 25, 2004

(65) Prior Publication Data

US 2005/0215782 A1  Sep. 29, 2005

(51) Int. Cl.
*C07D 501/24* (2006.01)
(52) U.S. Cl. ..................................... 540/215
(58) Field of Classification Search ..................... None
See application file for complete search history.

(56) References Cited

U.S. PATENT DOCUMENTS

| 2002/0099206 A1 | 7/2002 | Kameyama et al. | |
| 2004/0002600 A1* | 1/2004 | Deshpande et al. | 540/218 |

FOREIGN PATENT DOCUMENTS

| JP | 58-74689 | 5/1983 |
| JP | WO 99/10352 | 3/1999 |
| JP | 2004002451 A * | 1/2004 |

\* cited by examiner

*Primary Examiner*—Mark L. Berch
(74) *Attorney, Agent, or Firm*—Westerman, Hattori, Daniels & Adrian, LLP.

(57) ABSTRACT

A chlorinated azetidinone derivative expressed by Formula (1) and an alcoholate are allowed to react in a solvent containing at least one of alcohols and an ether at a pH of 8 or less. Thus a 3-chloromethyl-3-cephem derivative expressed by Formula (2) is prepared.

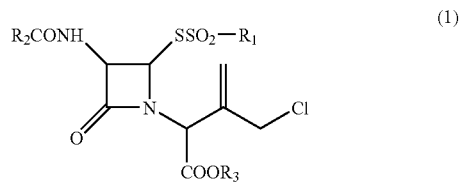

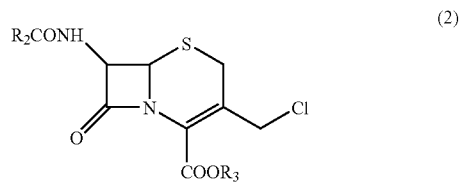

In the formulas, $R_1$ represents a substituted or unsubstituted aryl group or a substituted or unsubstituted heterocyclic residue, and $R_2$ and $R_3$ each represent a substituted or unsubstituted aromatic hydrocarbon group.

14 Claims, No Drawings

PROCESS FOR PREPARING CRYSTALLINE 3-CHLOROMETHYL-3-CEPHEM DERIVATIVES

BACKGROUND OF THE INVENTION

1. Field of the Invention

The present invention relates to process for preparing crystalline 3-chloromethyl-3-cephem derivatives, and particularly to process for preparing 3-chloromethyl-3-cephem derivatives expressed by Chemical Formula (2) in crystal form, which are useful as an intermediate for synthesizing 3-chloromethyl-3-cephem antibiotics.

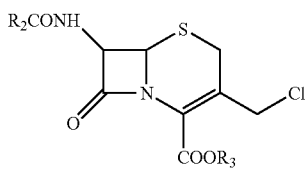

(2)

where $R_2$ and $R_3$ each represent a substituted or unsubstituted aromatic hydrocarbon group.

2. Description of the Related Art

The 3-chloromethyl-3-cephem derivatives expressed by Chemical Formula (2) are known as useful intermediates for synthesizing cephalosporin antibiotics, as disclosed in, for example, Japanese Unexamined Patent Application Publication Nos. 59-172493, 58-72591, 60-255796, 61-5084, 1-156984, and 1-308287, and International Patent Application Publication Nos. WO 99/10352 and WO 98/58932.

For the preparation of a 3-chloromethyl-3-cephem derivative expressed by Chemical Formula (2), for example, the acetoxy group of the acetoxymethyl group at the 3-position of a 3-acetoxymethylcephalosporin derivative is halogenated in the presence of a Lewis acid, such as boron trichloride (Tetrahedron Lett., p. 3991, 1974). In another process, a 2-azetidinone derivative prepared from penicillin G may be chlorinated by electrolysis and, then, cyclized to form a cephem derivative with a base (Tetrahedron Lett., 23, p. 2187, 1982). Also, Japanese Unexamined Patent Application Publication No. 4-66584 has disclosed a process in which a 7-substituted amino-3-hydroxymethyl-3-cephem-4-carbonate ester expressed by Chemical Formula (3) is allowed to react with a chlorinating agent in the presence of an alkaline-earth metal carbonate according to Reaction Formula (1):

Reaction Formula (1)

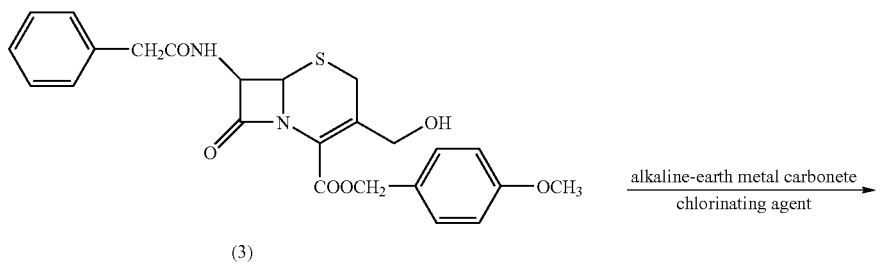

(3)

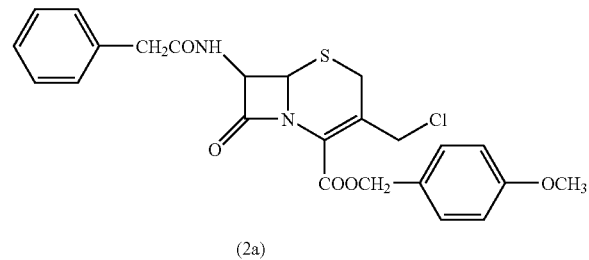

(2a)

Japanese Unexamined Patent Application Publication No. 58-74689 has disclosed a process in which an azetidinone derivative expressed by Chemical Formula (1a) is allowed to react in an organic solvent in the presence of a base according to Reaction Formula (2):

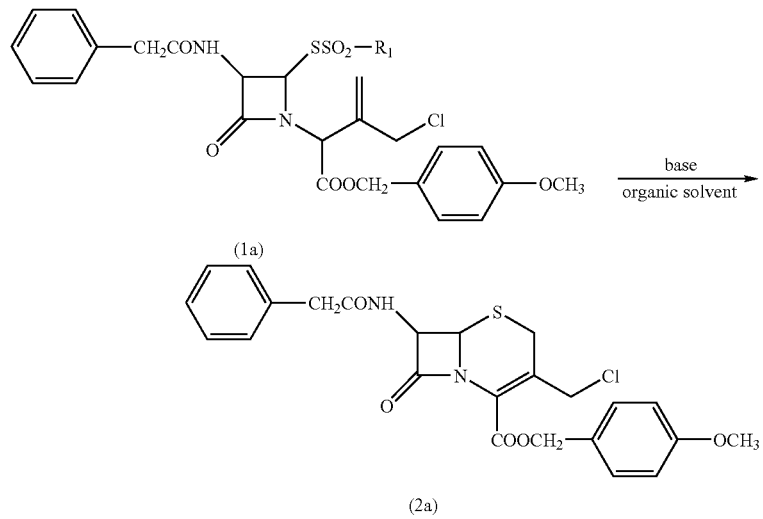

Among these processes, the process proposed by Japanese Unexamined Patent Application Publication No. 58-74689 provides 3-chloromethyl-3-cephem derivatives in oil form. In this process, dimethylformamide, which dissolves both the starting material azetidinone derivative expressed by Chemical Formula (1a) and the reaction product 3-chloromethyl-3-cephem derivative, is used as a reaction solvent, and the starting material is allowed to react with a base, weak alkaline ammonia or ammonia water, while the reaction product is prevented from being decomposed.

In this process, an alcohol, such as methanol, ethanol, or 2-propanol, may be used as the reaction solvent, and a metal hydroxide, such as strongly basic sodium hydroxide or potassium hydroxide, may be used as the base. However, since the alcohol does not dissolve the reaction product 3-chloromethyl-3-cephem derivative, the use of the alcohol does not provide the reaction product in oil form. In addition, the alcohol reacts with the base to produce water, which dissolves the base to increase the pH of the reaction system, that is, to make the reaction system alkaline. Consequently, the reaction product 3-chloromethyl-3-cephem derivative is decomposed by the alkali and thus, the yield is reduced.

Furthermore, 3-chloromethyl-3-cephem derivatives include a chlorine atom in their molecule, and are, consequently, instable in oil form. For example, the 3-chloromethyl-3-cephem derivatives release hydrochloric acid to decompose themselves during storage at room temperature, thus degrading the quality. Accordingly, such a 3-chloromethyl-3-cephem derivative is desired that is relatively stable for a long time in moderate conditions.

A process has been proposed in which a crystalline 3-chloromethyl-3-cephem derivative is prepared from an oil form.

For example, International Paten Application No. WO 99/10352 has proposed a process for preparing a crystalline 3-chloromethyl-3-cephem derivative by crystallizing an oily 3-chloromethyl-3-cephem derivative dissolved in dimethylformamide, with a cold alcohol or an alcohol-water mixture.

However, this process includes a complicated step of crystallizing an oily 3-chloromethyl-3-cephem derivative that has once been synthesized, and is thus disadvantageous in industrial production.

SUMMARY OF THE INVENTION

Accordingly, an object of the present invention is to provide an industrially advantageous process for preparing a crystalline 3-chloromethyl-3-cephem derivative useful as an intermediate for synthesizing cephalosporin antibiotics, the process which provides a highly pure crystalline 3-chloromethyl-3-cephem derivative with high yield by a reaction in a single step.

In view of the above-described disadvantages, the inventors of the present invention have conducted intensive research for a process for preparing a crystalline 3-chloromethyl-3-cephem derivative by a reaction in a single step. As a result, the inventors discovered a combination of starting materials, a chlorinated azetidinone derivative and an alcoholate, and a combination of solvents, an alcohol not dissolving the crystalline 3-chloromethyl-3-cephem derivative and an ether dissolving the chlorinated azetidinone derivative being a staring material and impurities or byproducts. Specifically, it was found that a highly pure crystalline 3-chloromethyl-3-cephem derivative expressed by Chemical Formula (2) can be provided with a high yield in a single step by a reaction using these combinations in the absence of water at a controlled pH.

In an aspect of the present invention, a crystalline 3-chloromethyl-3-cephem derivative is prepared by performing a reaction of a chlorinated azetidinone derivative with an alcoholate in a solvent containing an alcohol at a pH of 8 or less. The chlorinated azetidinone derivative is expressed by Chemical Formula (1):

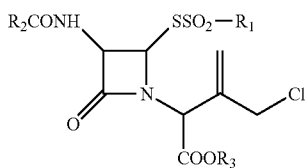

In Chemical Formula (1), $R_1$ represents a substituted or unsubstituted aryl group or a substituted or unsubstituted heterocyclic residue, and $R_2$ and $R_3$ each represent a substituted or unsubstituted aromatic hydrocarbon group. The 3-chloromethyl-3-cephem derivative is expressed by Chemical Formula (2):

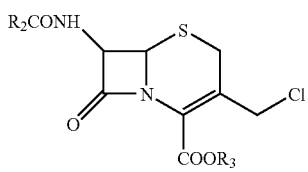

In Chemical Formula (2), $R_2$ and $R_3$ each represent a substituted or unsubstituted aromatic hydrocarbon group).

In another aspect of the present invention, a crystalline 3-chloromethyl-3-cephem derivative is prepared by performing a reaction of a chlorinated azetidinone derivative with an alcoholate in a solvent containing an alcohol and an ether at a pH of 8 or less. The chlorinated azetidinone derivative is expressed by Chemical Formula (1):

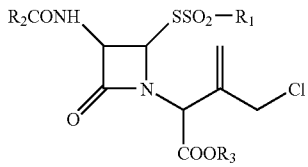

In Chemical Formula (1), $R_1$ represents is a substituted and unsubstituted aryl group or a substituted or unsubstituted heterocyclic residue, and $R_2$ and $R_3$ each represent a substituted or unsubstituted aromatic hydrocarbon group. The 3-chloromethyl-3-cephem derivative is expressed by Chemical Formula (2):

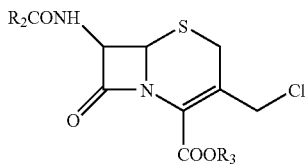

In the Chemical Formula (2), $R_2$ and $R_3$ each represent a substituted or unsubstituted aromatic hydrocarbon group.

For the reaction, preferably, solution A is prepared by dissolving the chlorinated azetidinone derivative in a solvent containing an ether; and solution B, by dissolving the alcoholate in a solvent containing an alcohol. The reaction is performed by adding solutions A and B into solution C containing an alcohol.

Preferably, part of solution A is first added to solution C, in an amount equivalent to 5 to 30 percent on a mole basis of the entire amount of the chlorinated azetidinone derivative involved in the reaction, and then the rest of solution A and solution B are simultaneously added to solution C.

Preferably, 0.8 to 1.5 mol of the alcoholate is allowed to react relative to 1 mol of the chlorinated azetidinone derivative.

Preferably, the alcohols are at least one of methanol and ethanol.

Preferably, the ether is dioxane.

Preferably, the alcoholate is sodium methylate or sodium ethylate.

Preferably, the reaction is performed at a temperature of 5° C. or less.

Preferably, solution A contains the chlorinated azetidinone derivative dissolved in a mixed solvent of dioxane and an alcohol.

Preferably, solution B contains alcoholate dissolved in an alcohol.

Preferably, solution C is a mixed solvent of an alcohol and dioxane.

Preferably, solution A and solution B are added by dripping.

Preferably, the reaction is performed in the absence of water.

Thus, the process of the present invention provide a highly pure crystalline 3-chloromethyl-3-cephem derivative useful as an intermediate for synthesizing cephalosporin antibiotics in an industrially advantageous single step with a high yield. The resulting crystalline 3-chloromethyl-3-cephem derivative is stabile for a long time under moderate conditions.

DESCRIPTION OF THE PREFERRED EMBODIMENTS

The present invention will now be described in detail.

The present invention provides a process for preparing a crystalline 3-chloromethyl-3-cephem derivative. In the process, a solution containing a chlorinated azetidinone derivative dissolved in a solvent containing an ether (hereinafter referred to as solution A) and a solution containing alcoholate dissolved in a solvent containing an alcohol (hereinafter referred to as solution B) are dripped into a solution containing an alcohol (hereinafter referred to as solution C) at a pH of 8 or less. The chlorinated azetidinone derivative is expressed by Chemical Formula (1): In the Chemical Formula (1), $R_1$ represents a substituted or unsubstituted aryl group or a substituted or unsubstituted heterocyclic residue, and $R_2$ and $R_3$ each represent a substituted or unsubstituted aromatic hydrocarbon group. The 3-chloromethyl-3-cephem derivative is expressed by Chemical Formula (2):

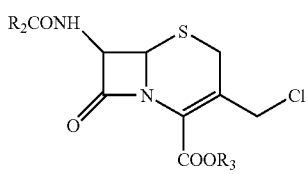

In Chemical Formula (2), $R_2$ and $R_3$ each represent a substituted or unsubstituted aromatic hydrocarbon group.

Preferably, solutions A and B are added in such proportions that 0.8 to 1.5 mol of the alcoholate is allowed to react relative to 1 mol of the chlorinated azetidinone derivative.

Preferably, the alcohol content in the total amount of the solvents after dripping solutions A and B is in the range of 30 to 95 percent by weight.

Preferably, part of solution A is first dripped into solution C, in an amount equivalent to 5 to 30 percent on a mole basis of the entire chlorinated azetidinone derivative involved in the reaction, and then the rest of solution A is dripped into solution C together with solution B.

Preferably, solution A contains the chlorinated azetidinone derivative dissolved in a mixed solvent of dioxane and an alcohol.

Preferably, solution B contains alcoholate dissolved in an alcohol.

Preferably, solution C is a mixed solvent of an alcohol and dioxane.

The crystalline 3-chloromethyl-3-cephem derivative of the present invention is prepared according to the following reaction formula:

Solutions A, B, and C used in the process of the present invention will now be described. Chlorinated azetidinone derivative:

$R_1$ of the starting material chlorinated azetidinone derivative (1) represents a substituted or unsubstituted aryl group or a substituted or unsubstituted heterocyclic residue. Exemplary aryl groups include phenyl, p-methylphenyl, p-methoxyphenyl, p-nitrophenyl, p-chlorophenyl, and pentachlorophenyl. Exemplary substituted or unsubstituted heterocyclic residues include 2-pyridyl, 2-benzothiazolyl, 1,3,4-thiadiazol-5-yl, 2-methyl-1,3,4-thiadiazol-5-yl, 1,2,3,4-tetrazol-5-yl, 1-methyl-1,2,3,4-tetrazol-5-yl, and 1-phenyl-1,2,3,4-tetrazol-5-yl.

$R_2$ and $R_3$ each represent a substituted or unsubstituted aromatic hydrocarbon group. Specifically, they may be benzyl, p-methoxybenzyl, phenyl, or p-tolyl. $R_2$ and $R_3$ may be the same or different.

The chlorinated azetidinone derivative expressed by Chemical Formula (1) may have a benzyl group as $R_2$ and a p-methoxybenzyl group as $R_3$, and this chlorinated azetidinone derivative, which is expressed by Chemical Formula (1a), can be prepared through two reaction steps expressed by following Reaction Formulas (3) and (4), using a thiazoline azetidinone derivative as a starting material (see Japanese Examined Patent Application Publication No. 6-9425, cited later).

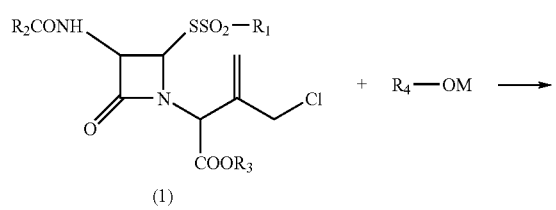

Reaction Formula (4)

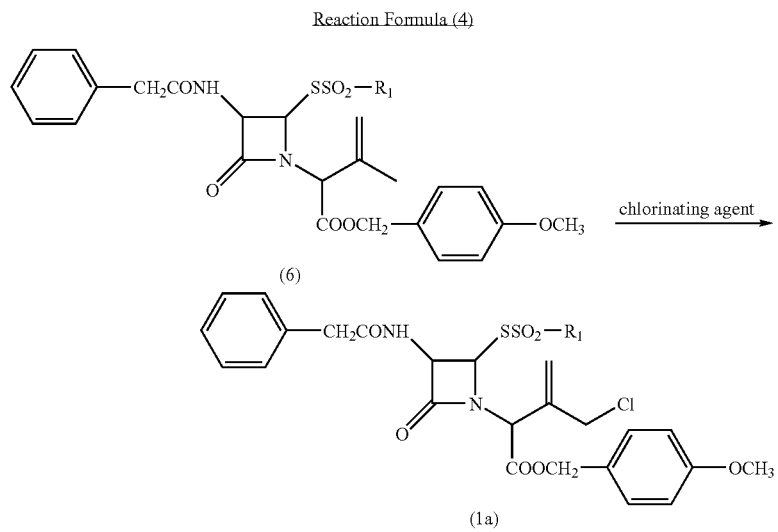

where $R_1$ represents the same as above.

Solution A:

Solution A containing a chlorinated azetidinone derivative may be prepared from a solution of the chlorinated azetidinone derivative expressed by Chemical Formula (1a) prepared according to Reaction Formula (4).

Solution A may also be prepared by dissolving the chlorinated azetidinone derivative expressed by Chemical Formula (1a) in a solvent so as to have a predetermined concentration.

Thus, solution A is prepared by dissolving a chlorinated azetidinone derivative expressed by Chemical Formula (1) in a solvent so as to have a predetermined concentration.

Exemplary solvents used for dissolving chlorinated azetidinone derivatives include esters, such as methyl formate, ethyl formate, methyl acetate, ethyl acetate, butyl acetate, and ethyl propionate; halogenated hydrocarbons, such as dichloromethane, chloroform, carbon tetrachloride, dichloroethane, dibromoethane, and chlorobenzene; ethers, such as diethyl ether, dibutyl ether, dioxane, and tetrahydrofuran; nitrites, such as acetonitrile and butyronitrile; and hydrocarbons, such as pentane, hexane, and cyclohexane. These solvents may be used singly or in combination. The solvent used for dissolving the chlorinated azetidinone derivative in solution A is hereinafter referred to as solvent A1. Among these solvents, dioxane is preferably used as solvent A1.

The solvent A1 content is in the range of 50 to 500 parts by weight, and preferably in the range of 100 to 500 parts by weight, relative to 100 parts by weight of the chlorinated azetidinone derivative expressed by Chemical Formula (1).

The solution of the chlorinated azetidinone derivative may be used by itself. However, it is preferable to add an alcohol capable of dissolving the chlorinated azetidinone derivative to the solution from the viewpoint of reducing the viscosity to enhance the ease of operation. This alcohol is hereinafter referred to as solvent A2. Exemplary alcohols used as solvent A2 include lower alcohols, such as methanol, ethanol, 1-propanol, and 2-propanol. These alcohols may be used singly or in combination. Among these lower alcohols, methanol or ethanol is preferably used because a reaction described later using methanol or ethanol can provide a highly pure crystalline 3-chloromethyl-3-cephem derivative with a high yield.

The alcohol (solvent A2) content is in the range of 100 to 500 parts by weight, and preferably in the range of 200 to 300 parts by weight, relative to 100 parts by weight of the chlorinated azetidinone derivative expressed by Chemical Formula (1).

Preferably, the chlorinated azetidinone derivative content in solution A is in the range of 0.05 to 1 mol/L, and more preferably in the range of 0.1 to 0.5 mol/L.

Solution B:

In the present invention, an alcoholate is used in crystallization.

The alcoholate is expressed by a chemical formula $R_4$-MO.

$R_4$ represents a straight or branched lower alkyl group having a carbon number in the range of 1 to 4, such as methyl, ethyl, isopropyl, or n-propyl. M represents an alkali metal, such as lithium, sodium, or potassium.

Exemplary alcoholates include sodium methylate, sodium ethylate, potassium methylate, potassium ethylate, lithium methylate, lithium ethylate, and potassium t-butylate. These alcoholates may be used singly or in combination.

Among these alcoholates, sodium methylate or sodium ethylate is preferably used.

Solution B containing such an alcoholate is prepared using a solvent capable of dissolving the alcoholate so as to have a predetermined concentration.

The solvent capable of dissolving the alcoholate is preferably at least one of alcohols, such as methanol, ethanol, 1-propanol, and 2-propanol. This solvent is hereinafter referred to as solvent B1. Among these alcohols, methanol or ethanol is preferably used as solvent B1.

Solution C:

Solution C containing an alcohol comprises the alcohol (hereinafter referred to as solvent C1) singly or in combination with another solvent (hereinafter referred to as solvent C2). Exemplary alcohols used as solvent C1 include lower alcohols such as methanol, ethanol, 1-propanol, and 2-propanol. These alcohols may be used singly or in combination. Among these alcohols, methanol or ethanol is preferably used.

While alcohols dissolve the starting material chlorinated azetidinone derivative expressed by Chemical Formula (1), it does not dissolve 3-chloromethyl-3-cephem derivatives expressed by Chemical Formula (2). Therefore, alcohols are suitable for recovering the reaction product in crystal form.

Solvent C2, which is used in combination with solvent C1 being an alcohol, dissolves the starting material chlorinated azetidinone derivative, and impurities after reaction, such as unreacted stating material and reaction byproducts, thus helping recover highly pure crystalline 3-chloromethyl-3-cephem derivatives expressed by Chemical Formula (2). Exemplary solvents C2 include esters, such as methyl formate, ethyl formate, methyl acetate, ethyl acetate, butyl acetate, and ethyl propionate; halogenated hydrocarbons, such as dichloromethane, chloroform, carbon tetrachloride, dichloroethane, dibromoethane, and chlorobenzene; ethers, such as diethyl ether, dibutyl ether, dioxane, and tetrahydrofuran; nitrites, such as acetonitrile and butyronitrile; and hydrocarbons, such as pentane, hexane, and cyclohexane. These solvents may be used singly or in combination. Among these solvents, dioxane is preferably used as solvent C2.

Solvent C2 content in the mixed solvent with solvent C1 or alcohol is in the range of 10 to 30 parts by weight relative to 100 parts by weight of solvent C1, and preferably in the range of 10 to 20 parts by weight. By performing the reaction in such proportions under conditions described below, a highly pure crystalline 3-chloromethyl-3-cephem derivative expressed by Chemical Formula (2) can be prepared with a high yield. A solvent C2 content of less than 10 parts by weight causes the crystals of the 3-chloromethyl-3-cephem derivative to increasingly hold impurities, such as reaction byproducts, to aggregate as the reaction proceeds. Thus, it becomes difficult to provide a highly pure 3-chloromethyl-3-cephem derivative with a high yield. A solvent C2 content of more than 30 parts by weight causes the crystalline 3-chloromethyl-3-cephem derivative to dissolve, thus undesirably reducing the yield.

Solution C containing an alcohol is preferably used in an amount in the range of 300 to 2,000 parts by weight, and more preferably in the range of 500 to 1,000 parts by weight, relative to 100 parts by weight of the chlorinated azetidinone derivative expressed by Chemical Formula (1). An amount of less than 300 parts by weight of solvent C makes the progress of the reaction difficult and allows unreacted material to be left. An amount of more than 2,000 parts by weight consumes an unnecessarily large amount of solvent, thus leading to industrial disadvantage.

Reaction Conditions:

In the process for preparing a 3-chloromethyl-3-cephem derivative expressed by Chemical Formula (2), a reaction is performed at an pH of 8 or less by dripping solution A containing the chlorinated azetidinone derivative expressed by Chemical Formula (1) and solution B containing the alcoholate into solution C containing an alcohol.

The reaction is performed at a pH of 8 or less, and preferably at a pH in the range of 6 to 8. A pH of more than 8 dissolves the crystals of the 3-chloromethyl-3-cephem derivative and, consequently, a desired crystalline 3-chloromethyl-3-cephem derivative is not provided with a high yield. Therefore, the pH is set at 8 or less.

Since the reaction proceeds rapidly, the pH is preferably measured with litmus paper or a pH meter. In use of the litmus paper, a drop is taken from the reaction system to the litmus paper and water is added to the drop. In use of the pH meter, a sample taken from the reaction system is diluted with water in an amount twice that of the sample, and the pH of the diluted sample is measured. The pH of the reaction system increases because unreacted part of the alcoholate is weak basic, and accordingly the reaction system becomes alkaline during the reaction.

Therefore, the pH is controlled in the above-described range during dripping solution A containing the chlorinated azetidinone derivative and solution B containing the alcoholate into solution C containing an alcohol.

Solution A and solution B are dripped in such proportions that the amount of the alcoholate is in the range of 0.8 to 1.5 times on a mole basis that of the chlorinated azetidinone derivative, and preferably in the range of 1.1 to 1.2 times, from the viewpoint of reducing the amount of the unreacted part of the starting material chlorinated azetidinone derivative. Thus, a highly pure crystalline 3-chloromethyl-3-cephem derivative can advantageously be obtained with a high yield. An amount of alcoholate of less than 0.8 times allows unnecessary amount of the chlorinated azetidinone derivative to remain unreacted. An amount of more than 1.5 times makes the reaction liquid alkali of more than pH 8, and consequently, the resulting crystalline 3-chloromethyl-3-cephem derivative is undesirably dissolved.

In addition, solution A and solution B are preferably dripped in such proportions that the total content of the alcohols (solvents A2, B1, and C1) in the total of the reaction solvents (solvents A1, A2, B1, C1, and C2) is in the range of 30 to 95 percent by weight after completion of dripping, and more preferably in the range of 60 to 90 percent by weight. An alcohol content in the solvents after dripping of less than 30 percent by weight makes it difficult to dissolve the alcoholate being a reactant, and causes the crystalline 3-chloromethyl-3-cephem derivative to dissolve, consequently reducing the yield. An alcohol content of more than 95 percent by weight does not allow impurities, such as reaction byproducts, to dissolve, and causes the crystals of the resulting 3-chloromethyl-3-cephem derivative to increasingly hold the impurities to aggregate as the reaction proceeds. Thus, it becomes difficult to provide a highly pure 3-chloromethyl-3-cephem derivative with a high yield.

Most preferably, solution A contains a mixed solvent for dissolving the chlorinated azetidinone derivative, constituted of dioxane (solvent A1) and at least one of methanol and ethanol (solvent B); solution B contains at least one of methanol and ethanol (solvent B1); and solution C contains a mixed solvent constituted of at least one of methanol and ethanol (solvent C1) and dioxane (solvent C2). These solutions are subjected to a reaction in such proportions that the total alcohol content in the total of solvents A1, A2, B1, C1, and C2 is in the range of 20 to 60 percent by weight after completion of the reaction, and preferably in the range of 30 to 50 percent by weight. Thus, a highly pure crystalline 3-chloromethyl-3-cephem derivative expressed by Chemical Formula (2) can be advantageously provided with a high yield.

For dripping solution A and solution B into solution C, the following two methods may be applied.

(1) Solution A and solution B is continuously or intermittently dripped into solution C in such a manner that solution A is ahead of solution B so as to control the pH of the reaction system in the above-described range.

(2) Part of solution A is first dripped into solution C, in an amount equivalent to 5 to 30 percent on a mole basis of the entire chlorinated azetidinone derivative involved in the reaction, and preferably in an amount equivalent to 10 to 20 percent, and then, the rest of solution A is dripped into solution C together with solution B so as to control the pH of the reaction system in the above-described range.

In the former method (1), solutions A and B are dripped into solution C in appropriate order so as to maintain the pH of the reaction system in the above-described range. In the latter method (2), a predetermined amount of solutions A is dripped into solution C in advance to make the reaction system acid (for example, pH 4), and then the rest of solution A and solution B are substantially simultaneously dripped into solution C in succession so as to maintain the pH of the reaction system in the above-described range.

In this instance, part of the chlorinated azetidinone derivative may be added to solution C in advance, in an amount of 5 to 30 percent on a mole basis of the entire azetidinone derivative involved in the reaction, and preferably in an amount of 10 to 30 percent. Then, necessary amounts of solution A and solution B are simultaneously dripped into solution C so as to maintain the pH of the reaction system in the above-described range.

The reaction product 3-chloromethyl-3-cephem derivative is extremely unstable against alkalis, and accordingly dissolves at a pH of 8 or more during the reaction. It is therefore preferable to drip solution A ahead of solution B to maintain the pH of the reaction system 8 or less, as described in the foregoing two dripping method because if solutions A and B are simultaneously dripped into solution C from the start, the reaction system is likely to become alkaline. Solution A has a pH of about 4, and adding solution B increases the pH of the reaction system.

Preferably, the latter method (2) is applied from the viewpoint of ease of pH control, that is, industrial advantage.

The entire amount of solution A may be added to the solution C, and then solution B may be dripped into solution C to perform the reaction at a pH of 8 or less. In this method, the crystals of the reaction product 3-chloromethyl-3-cephem derivative are liable to hold impurities, and thus the quality liable to be so degraded that a large load of purification is required in a subsequent step. However, the product can be provided in crystal form in a single step and the reaction can be allowed to proceed through a simple operation.

Solution A may be a solution resulting from a preceding step of chlorinating an azetidinone derivative to prepare the starting material chlorinated azetidinone derivative. This solution may be prepared by the process for chlorinating azetidinone derivatives disclosed in Japanese Examined Patent Application Publication No. 5-9425. By use of this solution, the targeted 3-chloromethyl-3-cephem derivative can be prepared from an azetidinone derivative through continuous steps.

A solution of the chlorinated azetidinone derivative in dioxane is preferably used as solution A. However, since dioxane has a melting point of 11° C., a reaction temperature of 10° C. or less may increase the viscosity of the solution or solidify the solution. In order to prevent increase in viscosity or solidification, methanol or ethanol may be added to reduce the viscosity so that the solution is easy to drip.

Preferably, the reaction is performed in a reaction system containing dioxane as a solvent. A low dioxane content allows the crystals of the reaction product 3-chloromethyl-3-cephem derivative to increasingly hold impurities, such as reaction byproducts, to aggregate as the reaction proceeds. It is therefore preferable that the dioxane content in the reaction system be set in the range of 10 to 30 parts by weight.

In the process of the present invention, the reaction proceeds in a nonaqueous solvent and does not produce water. Therefore, the alcoholate is not dissolved in water to act as an alkali. Thus, the process of the present invention advantageously helps prevent such an alkali from decomposing the reaction product crystalline 3-chloromethyl-3-cephem derivative.

Preferably, the reaction is performed at a temperature of 5° C. or less from the viewpoints of preventing byproducts and of producing the targeted crystalline 3-chloromethyl-3-cephem derivative expressed by Chemical Formula (2) with a high yield. However, a temperature of less than −20° C. causes the materials or impurities to precipitate. Accordingly, the reaction is preferably performed at a temperature in the range of −20 to 5° C., and more preferably in the range of −10 to 5° C.

The reaction solution becomes clouded gradually as the reaction proceeds and, thus, the targeted 3-chloromethyl-3-cephem derivative precipitates. After the completion of the reaction, the resulting liquid is neutralized, filtered, and dried to yield a crystalline product. The crystalline product may be purified by washing and recrystallization, if necessary.

Solvents used for washing and recrystallization include alcohols, such as methanol, ethanol, 1-propanol, and 2-propanol; nitrites, such as acetonitrile and butyronitrile; ketones, such as acetone and methyl ethyl ketone; and amides, such as dimethylformamide and diethylformamide. These solvents may be used singly or in combination.

In the process of the present invention, for example, a chlorinated azetidinone derivative expressed by Chemical Formula (1a) and an alcoholate expressed by Chemical Formula (7) are allowed to react to yield a targeted 3-chloromethyl-3-cephem derivative expressed by Chemical Formula (2a) and a byproduct metal sulfinate expressed by Chemical Formula (8) according to following Reaction Formula (5):

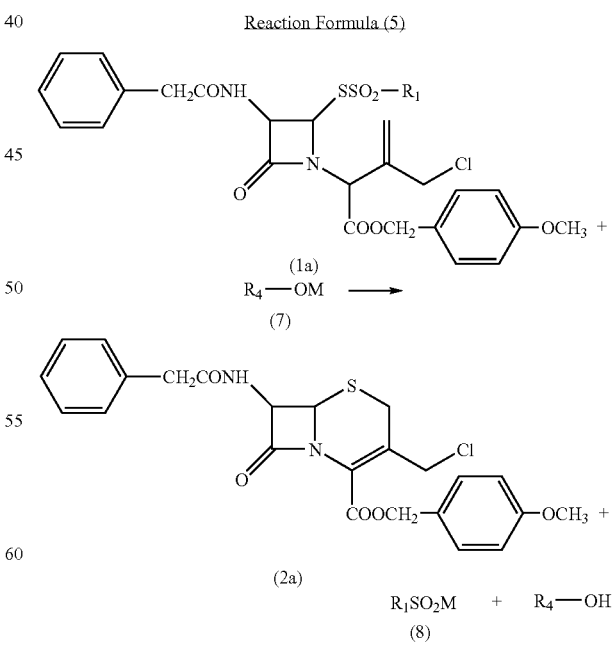

$R_1$ represents a substituted or unsubstituted aromatic hydrocarbon group; $R_4$, an organic group; and M, an alkali metal.

The metal sulfinate may be crystallized to separate from the mother liquor from which the crystalline 3-chloromethyl-3-cephem derivative has been collected. The separated metal sulfinate is allowed to react with bromine in a solvent to yield sulfonyl bromide. The sulfonyl bromide can be recycled as a raw material of the azetidinone derivative expressed by Chemical Formula (6) in Reaction Formula (3).

The crystalline 3-chloromethyl-3-cephem derivatives expressed by Chemical Formula (2) produced by the process of the present invention are stable for a long time under moderate conditions, and can be transformed into a 7-amino-3-chloromethyl-3-cephem derivative expressed by Chemical Formula (9), which is useful as cephalosporin antibiotics, according to following Reaction Formula (6):

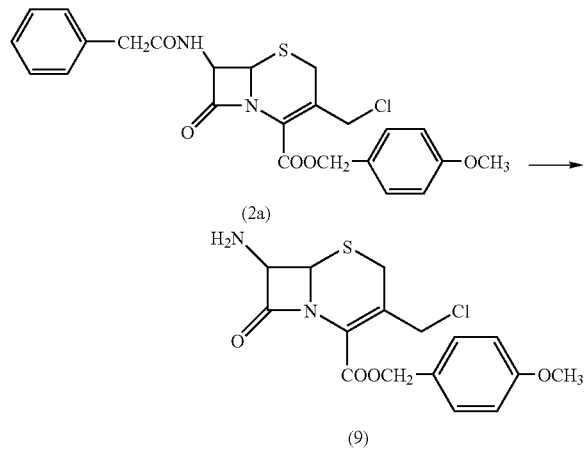

EXAMPLES

The present invention will now be further described with reference to examples, but it is not limited to the examples.

Example 1

A dropping funnel in which air was replaced with nitrogen was charged with 68.6 g of dioxane solution containing 47.7 percent by weight of the chlorinated azetidinone derivative expressed by Chemical Formula 10:

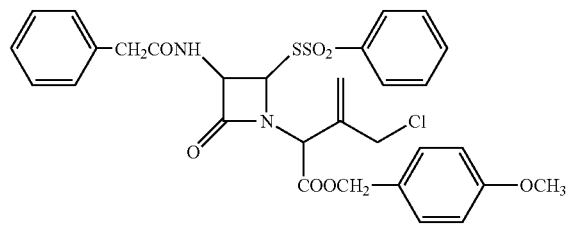

The dioxane solution was diluted with 50 g of dehydrated methanol (produced by Kanto Kagaku) to prepare solution A; hence, solution A contains 0.052 mol of the chlorinated azetidinone derivative.

A solution in an amount of 13.5 g containing 24 percent by weight of sodium methylate in pure methanol was diluted with 67.2 g of dehydrated methanol to prepare solution B containing 4 percent by weight (0.060 mol) of sodium methylate in methanol.

A four-neck reaction flask was charged with 13 g of dioxane and 160 mL of dehydrated ethanol, followed by cooling to −2 to 2° C. One-eighth of the entire amount of solution A was placed in the flask containing the cooled solvents. The resulting solution had a pH of 4.

While the temperature of the reaction system was maintained in the range of −2 to 2° C., solution A and solution B were simultaneously dripped into the flask. On dripping about one-eighth of solution B, the reaction liquid started to become clouded and formed slurry containing white crystals. While the temperature of the reaction system was maintained in the range of −2 to 2° C., solution A and solution B were simultaneously dripped into the slurry over a period of about 4 hours. The resulting reaction liquid had a pH in the range of 7 to 8. After the completion of dripping, the reaction was continued at 0° C. for another 0.25 hour with stirring.

After the completion of the reaction, 0.48 g of acetic acid was added to neutralize the resulting reaction liquid. The reaction liquid had a pH in the range of 4 to 5 after the neutralization. Then, the reaction liquid was stirred at −2 to 2° C. for 0.5 hour for ageing.

After ageing, the reaction liquid was filtered through a G3 glass filter. The resulting cake was rinsed with 18 g of ice-cold methanol, subsequently with 36 g of methanol solution containing 30% of water, and further with 18 g of ice-cold methanol.

The rinsed cake was dried in a desiccator with a vacuum pump at room temperature overnight. Thus, 22.9 g of a 3-chloromethyl-3-cephem derivative expressed by Chemical Formula (2a) was yielded (purity: 94.1%, yield: 85.1%).

Identification:
$^1$H-NMR($\delta$,CDCl$_3$) 3.41(1H, d, j=18.5), 3.59(1H, d, j=18.5), 4.92(1H, d, j=4.9), 5.82(1H, d, d, j=4.9,9.3), 6.12 (1H, d, j=9.3), 3.58(1H, d, j=16.1), 3.67(1H, d, j=16.1), 7.40–7.28(5H,m), 4.39(1H, d, j=11.9), 4.50(1H, d, j=11.9), 5.20(2H,s), 7.32(2H, d, j=8.6), 6.88(2H, d, j=8.6), 3.80(3H, s) FT-IR(cm$^{-1}$,KBr) 3449 cm$^{-1}$, 3271 cm$^{-1}$, 1778 cm$^{-1}$, 1703 cm$^{-1}$, 1645 cm$^{-1}$, 1251 cm$^{-1}$ FAB-MS M+1:487 m/z The resulting crystalline 3-chloromethyl-3-cephem derivative was subjected to X-ray diffraction with an X-ray diffractometer RINT 2400 produced by Rigaku, using copper radiation with a wavelength of 1.5418 Å passed through a monochromator filter. The results obtained from the X-ray diffraction pattern are shown in Table 1.

TABLE 1

| d | I/I$_0$ |
|---|---|
| 12.91 | 0.81 |
| 11.67 | 0.64 |
| 6.45 | 0.39 |
| 6.32 | 0.29 |
| 5.80 | 0.48 |
| 4.94 | 0.31 |
| 4.72 | 0.65 |
| 4.65 | 0.89 |
| 4.50 | 0.71 |
| 4.44 | 0.33 |
| 4.28 | 0.58 |
| 4.16 | 1.00 |
| 4.04 | 0.13 |

TABLE 1-continued

| d | I/I$_0$ |
|---|---|
| 3.97 | 0.15 |
| 3.85 | 0.71 |
| 3.77 | 0.50 |
| 3.70 | 0.11 |
| 3.45 | 0.46 |
| 3.37 | 0.20 |
| 3.20 | 0.13 |
| 3.16 | 0.18 |
| 3.09 | 0.12 |
| 2.90 | 0.13 |

In Table 1, d represents lattice spacing; I/I$_0$, relative intensity of a diffraction peak at d=4.17.

Example 2

A dropping funnel in which air was replaced with nitrogen was charged with 68.6 g of dioxane solution containing 47.7 percent by weight of the chlorinated azetidinone derivative expressed by Chemical formula 10. The dioxane solution was diluted with 50 g of dehydrated methanol (produced by Kanto Kagaku) to prepare solution A; hence, solution A contains 0.052 mol of the chlorinated azetidinone derivative.

In 103 g of methanol was dissolved 4.46 g (0.063 mol) of sodium ethylate to prepare solution B containing 4 percent by weight of sodium ethylate in methanol.

A four-neck reaction flask was charged with 13 g of dioxane and 160 mL of dehydrated ethanol, followed by cooling to −2 to 2° C. One-eighth of the entire amount of solution A was placed in the flask containing the cooled solvents. The resulting solution had a pH of 4.

While the temperature of the reaction system was maintained in the range of −2 to 2° C., solution A and solution B were simultaneously dripped into the flask. On dripping about one-fifth of solution B, the reaction liquid started to become clouded and formed slurry containing white crystals. While the temperature of the reaction system was maintained in the range of −2 to 2° C., solution A and solution B were simultaneously dripped into the slurry over a period of about 4 hours. The resulting reaction liquid had a pH in the range of 7 to 8. After the completion of dripping, the reaction was continued at 0° C. for another 0.25 hour with stirring.

After the completion of the reaction, 0.44 g of acetic acid was added to neutralize the resulting reaction liquid. The reaction liquid had a pH in the range of 4 to 5 after the neutralization. Then, the reaction liquid was stirred at −2 to 2° C. for 0.5 hour for ageing.

After ageing, the reaction liquid was filtered through a G3 glass filter. The resulting cake was rinsed with 18 g of ice-cold methanol, subsequently with 36 g of methanol solution containing 30% of water, and further with 18 g of ice-cold methanol.

The rinsed cake was dried in a desiccator with a vacuum pump at room temperature overnight. Thus, 21.8 g of a 3-chloromethyl-3-cephem derivative expressed by Chemical Formula (2a) was yielded (purity: 94.3%, yield: 81.2%).

Identification:
$^1$H-NMR (δ,CDCl$_3$) 3.41(1H, d, j=18.5), 3.59(1H, d, j=18.5), 4.92(1H, d, j=4.9), 5.82(1H, d, d, j=4.9,9.3),6.12 (1H, d, j=9.3), 3.58(1H, d, j=16.1), 3.67(1H, d, j=16.1), 7.40–7.28(5H,m), 4.39(1H, d, j=11.9), 4.50(1H, d, j=11.9), 5.20(2H,s), 7.32(2H, d, j=8.6), 6.88(2H, d, j=8.6), 3.80(3H, s) FT-IR(cm$^{-1}$,KBr) 3449 cm$^{-1}$, 3271 cm$^{-1}$, 1778 cm$^{-1}$, 1703 cm$^{-1}$, 1645 cm$^{-1}$, 1251 cm$^{-1}$ FAB-MS M+1:487 m/z The resulting 3-chloromethyl-3-cephem derivative was subjected to X-ray diffraction, and the obtained X-ray diffraction pattern was similar to that of the Example 1.

Example 3

A dropping funnel in which air was replaced with nitrogen was charged with 69.75 g of dioxane solution containing 46.9 percent by weight of the chlorinated azetidinone derivative expressed by Chemical Formula 10. The dioxane solution was diluted with 50 g of dehydrated methanol (produced by Kanto Kagaku) to prepare solution A; hence, solution A contains 0.052 mol of the chlorinated azetidinone derivative.

In 103 g of dehydrated ethanol was dissolved 4.46 g (0.063 mol) of sodium ethylate to prepare solution B containing 4 percent by weight of sodium ethylate in ethanol.

A four-neck reaction flask was charged with 13 g of dioxane and 160 mL of dehydrated ethanol, followed by cooling to −2 to 2° C. One-eighth of the entire amount of solution A was placed in the flask containing the cooled solvents. The resulting solution had a pH of 4.

While the temperature of the reaction system was maintained in the range of −2 to 2° C., solution A and solution B were simultaneously dripped into the flask. On dripping about one-fourth of solution B, the reaction liquid started to become clouded and formed slurry containing white crystals. While the temperature of the reaction system was maintained in the range of −2 to 2° C., solution A and solution B were simultaneously dripped into the slurry over a period of about 4 hours. The resulting reaction liquid had a pH in the range of 7 to 8. After the completion of dripping, the reaction was continued at 0° C. for another 0.25 hour with stirring.

After the completion of the reaction, 0.43 g of acetic acid was added to neutralize the resulting reaction liquid. The reaction liquid had a pH in the range of 4 to 5 after the neutralization. Then, the reaction liquid was stirred at −2 to 2° C. for 0.5 hour for ageing.

After ageing, the reaction liquid was filtered through a G3 glass filter. The resulting cake was rinsed with 18 g of ice-cold methanol, subsequently with 36 g of methanol solution containing 30% of water, and further with 18 g of ice-cold methanol.

The rinsed cake was dried in a desiccator with a vacuum pump at room temperature overnight. Thus, 23.28 g of a 3-chloromethyl-3-cephem derivative expressed by Chemical Formula (2a) was yielded (purity: 91.6%, yield: 84.2%).

Identification:
$^1$H-NMR(δ,CDCl$_3$) 3.41(1H, d, j=18.5), 3.59(1H, d, j=18.5), 4.92(1H, d, j=4.9), 5.82(1H, d, d, j=4.9,9.3), 6.12 (1H, d, j=9.3), 3.58(1H, d, j=16.1), 3.67(1H, d, j=16.1), 7.40–7.28(5H,m), 4.39(1H, d, j=11.9), 4.50(1H, d, j=11.9), 5.20(2H,s), 7.32(2H, d, j=8.6), 6.88(2H, d, j=8.6), 3.80(3H, s) FT-IR(cm$^{-1}$,KBr) 3449 cm$^{-1}$, 3271 cm$^{-1}$, 1778 cm$^{-1}$, 1703 cm$^{-1}$, 1645 cm$^{-1}$, 1251 cm$^{-1}$ M+1:487 m/z The resulting 3-chloromethyl-3-cephem derivative was subjected to X-ray diffraction, and the obtained X-ray diffraction pattern was similar to that of the Example 1.

Example 4

A dropping funnel in which air was replaced with nitrogen was charged with 64.55 g of dioxane solution containing 50.6 percent by weight of the chlorinated azetidinone derivative expressed by Chemical Formula 10. The dioxane solution was diluted with 50 g of dehydrated methanol (produced by Kanto Kagaku) to prepare solution A; hence solution A contains 0.052 mol of the chlorinated azetidinone derivative.

A solution in an amount of 13.5 g containing 24 percent by weight of sodium methylate in pure methanol was diluted with 67.2 g of dehydrated methanol to prepare solution B containing 4 percent by weight (0.060 mol) of sodium methylate in methanol.

A reaction flask was charged with 13 g of dioxane and 160 mL of dehydrated methanol, followed by cooling to −2 to 2° C. One-eighth of the entire amount of solution A was placed in the flask containing the cooled solvents. The resulting solution had a pH of 4.

While the temperature of the reaction system was maintained in the range of −2 to 2° C., solution A and solution B were simultaneously dripped into the flask. On dripping about one-fourth of solution B, the reaction liquid started to become clouded and formed slurry containing white crystals. Simultaneous dripping of solutions A and B was continued for about 2 hours. The resulting reaction liquid had a pH in the range of 7 to 8. After the completion of dripping, the reaction was continued at 0° C. for another 0.25 hour with stirring.

After the completion of the reaction, 0.48 g of acetic acid was added to neutralize the resulting reaction liquid. The reaction liquid had a pH in the range of 4 to 5 after the neutralization. Then, the reaction liquid was stirred at −2 to 2° C. for 0.5 hour for ageing.

After ageing, the reaction liquid was filtered through a G3 glass filter. The resulting cake was rinsed with 18 g of ice-cold methanol, subsequently with 36 g of methanol solution containing 30% of water, and further with 18 g of ice-cold methanol.

The rinsed cake was dried in a desiccator with a vacuum pump at room temperature overnight. Thus, 22.58 g of a 3-chloromethyl-3-cephem derivative expressed by Chemical Formula (2a) was yielded (purity: 94.4%, yield: 84.2%).

Identification:
$^1$H-NMR($\delta$,CDCl$_3$) 3.41(1H, d, j=18.5), 3.59(1H, d, j=18.5), 4.92(1H, d, j=4.9), 5.82(1H, d, d, j=4.9,9.3), 6.12 (1H, d, j=9.3), 3.58(1H, d, j=16.1), 3.67(1H, d, j=16.1), 7.40–7.28(5H,m), 4.39(1H, d, j=11.9), 4.50(1H, d, j=11.9), 5.20(2H,s), 7.32(2H, d, j=8.6), 6.88(2H, d, j=8.6), 3.80(3H, s) FT-IR(cm$^{-1}$,KBr) 3449 cm$^{-1}$, 3271 cm$^{-1}$, 1778 cm$^{-1}$, 1703 cm$^{-1}$, 1645 cm$^{-1}$, 1251 cm$^{-1}$ FAB-MS M+1:487 m/z The resulting 3-chloromethyl-3-cephem derivative was subjected to X-ray diffraction, and the obtained X-ray diffraction pattern was similar to that of the Example 1.

Example 5

A dropping funnel in which air was replaced with nitrogen was charged with 57.4 g of dioxane solution containing 57.6 percent by weight of the chlorinated azetidinone derivative expressed by Chemical Formula 10. The dioxane solution was diluted with 50 g of dehydrated methanol (produced by Kanto Kagaku) to prepare solution A; hence solution A contains 0.052 mol of the chlorinated azetidinone derivative.

A solution in an amount of 13.5 g containing 24 percent by weight of sodium methylate in pure methanol was diluted with 67.0 g of dehydrated methanol to prepare solution B containing 4 percent by weight (0.060 mol) of sodium methylate in methanol.

A four-neck reaction flask in which air was replaced with nitrogen was charged with 12.9 g of dioxane and 160 mL of dehydrated ethanol, followed by cooling to −2 to 2° C. The entirety of solution A was added to the flask containing the cooled solvents. The resulting solution had a pH of 4.

Then, while the temperature of the reaction system was maintained in the range of −2 to 2° C., solution B was dripped into the flask for over a period of about 2 hours. On dripping about one-third of solution B, the reaction liquid started to become clouded and formed slurry containing white crystals. The reaction liquid had a pH of 8 just after the completion of dripping. Subsequently, the reaction was continued at 0° C. for another 0.25 hour with stirring.

After the completion of the reaction, 0.40 g of acetic acid was added to neutralize the resulting reaction liquid. The reaction liquid had a pH in the range of 4 to 5 after the neutralization. Then, the reaction liquid was stirred at −2 to 2° C. for 0.5 hour for ageing.

After ageing, the reaction liquid was filtered through a G3 glass filter. The resulting cake was rinsed with 18 g of ice-cold methanol, subsequently with 36 g of methanol solution containing 30% of water, and further with 18 g of ice-cold methanol.

The rinsed cake was dried in a desiccator with a vacuum pump at room temperature overnight. Thus, 20.50 g of a 3-chloromethyl-3-cephem derivative expressed by Chemical Formula (2a) was yielded (purity: 92.0%, yield: 74.5%).

Identification:
$^1$H-NMR ($\delta$,CDCl$_3$) 3.41(1H, d, j=18.5), 3.59(1H, d, j=18.5), 4.92(1H, d, j=4.9), 5.82(1H, d, d, j=4.9,9.3), 6.12 (1H, d, j=9.3), 3.58(1H, d, j=16.1), 3.67(1H, d, j=16.1), 7.40–7.28(5H,m), 4.39(1H, d, j=11.9), 4.50(1H, d, j=11.9), 5.20(2H,s), 7.32(2H, d, j=8.6), 6.88(2H, d, j=8.6), 3.80(3H, s) FT-IR(cm$^{-1}$,KBr) 3449 cm$^{-1}$, 3271 cm$^{-1}$, 1778 cm$^{-1}$, 1703 cm$^{-1}$, 1645 cm$^{-1}$, 1251 cm$^{-1}$ FAB-MS M+1:487 m/z Comparative Example 1

A dropping funnel in which air was replaced with nitrogen was charged with 65.8 g of dioxane solution containing 49.7 percent by weight of the chlorinated azetidinone derivative expressed by Chemical Formula 10. The dioxane solution was diluted with 50 g of dehydrated methanol (produced by Kanto Kagaku) to prepare solution A; hence solution A contains 0.052 mol of the chlorinated azetidinone derivative.

A solution in an amount of 17.0 g containing 24 percent by weight of sodium methylate in pure methanol was diluted with 85.0 g of dehydrated methanol to prepare solution B containing 4 percent by weight (0.076 mol) of sodium methylate in methanol.

A four-neck reaction flask was charged with 13 g of dioxane and 160 mL of dehydrated ethanol, followed by cooling to −2 to 2° C. One-eighth of the entire amount of solution A was placed in the flask containing the cooled solvents. The resulting solution had a pH of 4.

While the temperature of the reaction system was maintained in the range of −2 to 2° C., solution A and solution B were simultaneously dripped into the flask. On dripping about one-fifth of solution B, the reaction liquid started to become clouded and formed slurry containing white crystals. Simultaneous dripping of solutions A and B was continued for about 4 hours, and the entire amount of solution A was added. At this moment, the amount of solution B that had been dripped was 80.4 g, and the pH of the reaction liquid was 7 to 8. The entire amount of the rest of solution B, about 20 g, was dripped over a period of 30 minutes. The reaction liquid turned reddish brown. The reaction liquid had a pH of 10 just after the completion of dripping. The reaction was continued at 0° C. for another 0.25 hour with stirring.

After the completion of the reaction, 0.64 g of acetic acid was added to neutralize the resulting reaction liquid. The reaction liquid had a pH in the range of 4 to 5 after the neutralization. Then, the reaction liquid was stirred at −2 to 2° C. for 0.5 hour for ageing.

After ageing, the reaction liquid was filtered through a G3 glass filter. The resulting cake was rinsed with 18 g of ice-cold methanol, subsequently with 36 g of methanol solution containing 30% of water, and further with 18 g of ice-cold methanol.

The rinsed cake was dried in a desiccator with a vacuum pump at room temperature overnight. Thus, 18.07 g of a 3-chloromethyl-3-cephem derivative expressed by Chemical Formula (2a) was yielded (purity: 85.9%, yield: 61.3%).

Comparative Example 2

In 640 mL of dried dimethylformamide (DMF) was dissolved 71.48 g (0.104 mol) of the 3-chloromethyl-3-cephem derivative expressed by Chemical Formula (10), in an atmosphere of nitrogen, followed by cooling to −30° C. Then, 17.76 g of 28% ammonia water (0.292 mol of ammonia) was dripped into the DMF solution of the chlorinated azetidinone derivative at a temperature in the range of −30 to −20° C.; hence, the amount of ammonia added was 2.8 times that of the chlorinated azetidinone derivative on a mole basis. After dripping, the reaction liquid was aged for 1 hour at a temperature in the range of −30 to −20° C.

Then, 5% hydrochloric acid solution was added to the reaction liquid to set the pH in the range of 4 to 5, and subsequently 1.92 L of ethyl acetate was added. The resulting organic phase was separated out at 0° C. The separated organic phase was washed twice with a saturated salt solution, and was then dehydrated by adding anhydrous sodium sulfate.

The dehydrated organic phase was concentrated under reduced pressure to yield 38.0 g of an oily 3-chloromethyl-3-cephem derivative expressed by Chemical Formula (2a) (purity: 93.3%, yield: 70.0%).

Identification:
$^1$H-NMR($\delta$,CDCl$_3$) 3.41(1H, d, j=18.5), 3.59(1H, d, j=18.5), 4.92(1H, d, j=4.9), 5.82(1H, d, d, j=4.9,9.3), 6.12 (1H, d, j=9.3), 3.58(1H, d, j=16.1), 3.67(1H, d, j=16.1), 7.40–7.28(5H,m), 4.39(1H, d, j=11.9), 4.50(1H, d, j=11.9), 5.20(2H,s), 7.32(2H, d, j=8.6), 6.88(2H, d, j=8.6), 3.80(3H, s) FT-IR(cm$^{-1}$,KBr) 3449 cm$^{-1}$, 3271 cm$^{-1}$, 1778 cm$^{-1}$, 1703 cm$^{-1}$, 1645 cm$^{-1}$, 1251 cm$^{-1}$ FAB-MS M+1:487 m/z Comparative Example 3

In 28 mL of DMF was dissolved 10.0 g of the oily 3-chloromethyl-3-cephem derivative prepared in Comparative Example 2.

The DMF solution of the oily 3-chloromethyl-3-cephem derivative was slowly dripped at 3 to 5° C. into 400 mL of methanol cooled to 3° C., thereby precipitating a crystalline 3-chloromethyl-3-cephem derivative.

After solid-liquid separation, the collected crystalline 3-chloromethyl-3-cephem derivative was rinsed with methanol, and subsequently dried under reduced pressure to yield 8.62 g of the crystals of the 3-chloromethyl-3-cophem derivative (purity: 94.0%, recovery factor: 86.2%, yield on the basis of the staring material of Comparative Example 2: 60.3%)

Identification:
$^1$H-NMR($\delta$,CDCl$_3$) 3.41(1H, d, j=18.5), 3.59(1H, d, j=18.5), 4.92(1H, d, j=4.9), 5.82(1H, d, d, j=4.9,9.3), 6.12 (1H, d, j=9.3), 3.58(1H, d, j=16.1), 3.67(1H, d, j=16.1), 7.40–7.28(5H,m), 4.39(1H, d, j=11.9), 4.50(1H, d, j=11.9), 5.20(2H,s), 7.32(2H, d, j=8.6), 6.88(2H, d, j=8.6), 3.80(3H, s) FT-IR(cm$^{-1}$,KBr) 3449 cm$^{-1}$, 3271 cm$^{-1}$, 1778 cm$^{-1}$, 1703 cm$^{-1}$, 1645 cm$^{-1}$, 1251 cm$^{-1}$ FAB-MS M+1:487 m/z The resulting 3-chloromethyl-3-cephem derivative was subjected to X-ray diffraction in the same manner as in Example 1. The results obtained from the X-ray diffraction pattern are shown in Table 2.

TABLE 2

| d | I/I$_0$ |
|---|---|
| 12.95 | 0.61 |
| 11.68 | 0.51 |
| 9.91 | 0.10 |
| 6.47 | 0.63 |
| 6.33 | 0.24 |
| 5.81 | 0.62 |
| 4.96 | 0.47 |
| 4.73 | 0.70 |
| 4.66 | 0.72 |
| 4.51 | 0.67 |
| 4.44 | 0.31 |
| 4.29 | 0.56 |
| 4.17 | 1.00 |
| 4.05 | 0.25 |
| 3.98 | 0.17 |
| 3.86 | 0.74 |
| 3.78 | 0.47 |
| 3.70 | 0.14 |
| 3.56 | 0.07 |
| 3.54 | 0.06 |
| 3.45 | 0.54 |
| 3.37 | 0.20 |
| 3.29 | 0.14 |
| 3.22 | 0.20 |
| 3.20 | 0.15 |
| 3.16 | 0.20 |
| 3.09 | 0.18 |
| 2.90 | 0.22 |
| 2.85 | 0.10 |
| 2.68 | 0.14 |
| 2.60 | 0.16 |
| 2.58 | 0.11 |
| 2.50 | 0.10 |
| 2.49 | 0.13 |

In Table 2, d represents lattice spacing; I/I$_0$, relative intensity of a diffraction peak at d=4.17.

Comparative Example 4

In 135 g of methanol was dissolved 35.74 g (0.052 mol) of the 3-chloromethyl-3-cephem derivative expressed by Chemical Formula (10), in an atmosphere of nitrogen, followed by cooling to −5° C. Then, a solution of 12.5% of potassium hydroxide in ethanol containing 20% of water was dripped in an amount of 35.0 g into the methanol solution of the chlorinated azetidinone derivative at a temperature in the range of −5 to −2° C.; hence, the amount of potassium hydroxide added was 0.078 mol or 1.5 times that of the chlorinated azetidinone derivative on a mole basis. After dripping, the reaction system was aged for 1 hour at a temperature in the range of −2 to 0° C. The reaction liquid had a pH of 9 after ageing. Then, acetic acid was added to the reaction liquid to set the pH in the range of 4 to 5, and the reaction liquid was stirred at −2 to 2° C. for 0.5 hour for ageing. After ageing, the reaction liquid was filtered through a G3 glass filter. The resulting cake was rinsed with 18 g of ice-cold methanol, subsequently with 36 g of methanol solution containing 30% of water, and further with ice-cold methanol. The rinsed cake was dried in a desiccator with a vacuum pump at room temperature overnight. Thus, 15.15 g of a yellowish brown 3-chloromethyl-3-cephem derivative expressed by Chemical Formula (2a) was yielded (purity: 51.3%, yield: 30.7%).

Stability Test:

The 3-chloromethyl-3-cephem derivatives prepared in Examples 1 to 5 and Comparative Examples 1 to 4 in an amount of 5 g were each placed in a sealed beaker and allowed to stand in a thermostatic chamber at 25° C. for 30 days.

Then, the purity of each sample of the 3-chloromethyl-3-cephem derivatives was measured. The results are shown in Table 3.

TABLE 3

|  | Purity before stability test | Purity after 30 days |
| --- | --- | --- |
| Example 1 | 94.1 | 94.1 |
| Example 2 | 94.3 | 94.3 |
| Example 3 | 91.6 | 91.6 |
| Example 4 | 94.4 | 94.4 |
| Example 5 | 92.0 | 92.0 |
| Comparative example 1 | 85.9 | 85.9 |
| Comparative example 2 | 93.3 | 89.9 |
| Comparative example 3 | 94.0 | 94.0 |
| Comparative example 4 | 51.3 | 46.5 |

The invention claimed is:

1. A process for preparing a crystalline 3-chloromethyl-3-cephem derivative, comprising a reaction step of performing a reaction of a chlorinated azetidinone derivative with an alcoholate, in a solvent containing at least one alcohol, and at a pH of 8 or less, wherein the chlorinated azetidinone derivative is expressed by Chemical Formula (1):

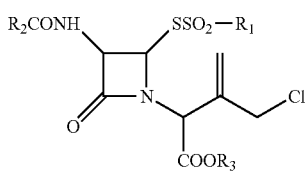

where $R_1$ represents one selected from the group consisting of substituted and unsubstituted aryl groups and substituted and unsubstituted heterocyclic residues, and $R_2$ and $R_3$ each represent one selected from the group consisting of substituted and unsubstituted aromatic hydrocarbon groups, and wherein the 3-chloromethyl-3-cephem derivative is expressed by Chemical Formula (2):

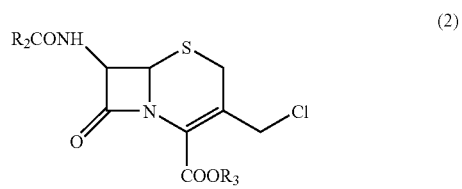

where $R_2$ and $R_3$ each represent one selected from the group consisting of substituted and unsubstituted aromatic hydrocarbon groups.

2. A process for preparing a crystalline 3-chloromethyl-3-cephem derivative, comprising the a reaction step of performing a reaction of a chlorinated azetidinone derivative with an alcoholate, in a solvent containing at least one alcohol and at least one ether, and at a pH of 8 or less, wherein the chlorinated azetidinone derivative is expressed by Chemical Formula (1):

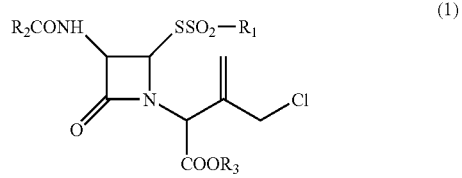

where $R_1$ represents one selected from the group consisting of substituted and unsubstituted aryl groups and substituted and unsubstituted heterocyclic residues, and $R_2$ and $R_3$ each represent one selected from the group consisting of substituted and unsubstituted aromatic hydrocarbon groups, and wherein the 3-chloromethyl-3-cephem derivative is expressed by Chemical Formula (2):

where $R_2$ and $R_3$ each represent one selected from the group consisting of substituted and unsubstituted aromatic hydrocarbon groups.

3. The process according to claim 1 or 2, wherein the reaction step is performed by adding solution A containing the chlorinated azetidinone derivative and solution B containing the alcoholate into solution C containing said solvent, and wherein the chlorinated azetidinone derivative in solution A is dissolved in a solvent containing at least one ether, and the alcoholate in solution B is dissolved in a solvent containing at least one alcohol.

4. The process according to claim 3, wherein part of solution A in an amount equivalent to 5 to 30 percent on a mole basis of the entire amount of chlorinated azetidinone derivative involved in the reaction is added to solution C, and then the rest of solution A and solution B are simultaneously added to solution C.

5. The process according to claim 1 or 2, wherein 0.8 to 1.5 mol of the alcoholate is allowed to react relative to 1 mol of the chlorinated azetidinone derivative.

6. The process according to claim 1 or 2, wherein said at least one alcohol is at least one selected from the group consisting of methanol and ethanol.

7. The process according to claim 2, wherein the ether is dioxane.

8. The process according to claim 1 or 2, wherein the alcoholate is at least one selected from the group consisting of sodium methylate and sodium ethylate.

9. The process according to claim 1 or 2, wherein the reaction is performed at a temperature of 5° C. or less.

10. The process according to claim 1,
wherein the reaction step is performed by adding solution A containing the chlorinated azetidinone derivative and solution B containing the alcoholate into solution C containing said solvent, wherein
the chlorinated azetidinone derivative in solution A is dissolved in a solvent containing at least one alcohol and dioxane, and
the alcoholate in solution B is dissolved in a solvent containing at least one alcohol.

11. The process according to claim 3, wherein solution C further contains dioxane.

12. The process according to claim 3, wherein solution A and solution B are added by dripping.

13. The process according to claim 1 or 2, wherein the reaction is performed in the absence of water.

14. The process according to claim 2,
wherein the reaction step is performed by adding solution A containing the chlorinated azetidinone derivative and solution B containing the alcoholate into solution C containing said solvent, wherein
the chlorinated azetidinone derivative in solution A is dissolved in a solvent containing at least one alcohol and dioxane,
the alcoholate in solution B is dissolved in a solvent containing at least one alcohol, and
in said solvent containing at least one alcohol and an ether the ether is dioxane.

* * * * *